United States Patent
Von Wallfeld et al.

(10) Patent No.: US 6,215,096 B1
(45) Date of Patent: Apr. 10, 2001

(54) METHOD FOR DETERMINING A REQUIRED SHAPE FOR AT LEAST ONE SURFACE OF AN ARTIFICIAL OR NATURAL PART OF AN EYE WHICH IS INTERSECTED BY A PATH OF RAYS THROUGH THE PUPIL OF THE EYE, AND DEVICE FOR THE MANUFACTURE OF AN ARTIFICIAL LENS

(75) Inventors: Herbert Von Wallfeld, Jülich; Thomas Neuhann, Müchen, both of (DE)

(73) Assignee: Technomed Gesellschaft für Med. und Med.-Techn. Systeme mbH, Baesweiler (DE)

( * ) Notice: Subject to any disclaimer, the term of this patent is extended or adjusted under 35 U.S.C. 154(b) by 0 days.

(21) Appl. No.: 09/341,928

(22) PCT Filed: Jan. 14, 1998

(86) PCT No.: PCT/DE98/00102

§ 371 Date: Oct. 5, 1999

§ 102(e) Date: Oct. 5, 1999

(87) PCT Pub. No.: WO98/31299

PCT Pub. Date: Jul. 23, 1998

(30) Foreign Application Priority Data

Jan. 21, 1997 (DE) .............................................. 197 01 807
Jun. 26, 1997 (DE) .............................................. 197 27 121

(51) Int. Cl.[7] .................................................... B23K 26/00

(52) U.S. Cl. ................................ 219/121.68; 219/121.69; 219/121.67; 219/121.73

(58) Field of Search ........................ 219/121.68, 121.69, 219/121.67, 121.73, 121.76, 121.6, 121.72; 623/4, 5, 6; 216/65, 63

(56) References Cited

U.S. PATENT DOCUMENTS

| | | | |
|---|---|---|---|
| 4,154,114 | * | 5/1979 | Katz et al. .............................. 73/629 |
| 4,434,581 | * | 3/1984 | Spriggs ..................................... 51/67 |
| 4,721,379 | | 1/1988 | L'Esperance . |

(List continued on next page.)

FOREIGN PATENT DOCUMENTS

| | | |
|---|---|---|
| 8 21 131 | 9/1951 | (DE) . |
| 100 392 | 9/1973 | (DE) . |
| 196 34 50 B2 | 5/1981 | (DE) . |
| 42 10 384 A1 | 10/1993 | (DE) . |
| 43 25 494 A1 | 7/1994 | (DE) . |
| 44 40 573 | 5/1996 | (DE) . |
| 195 38 567 | 4/1997 | (DE) . |

(List continued on next page.)

Primary Examiner—Patrick Ryan
Assistant Examiner—M. Alexandra Elve
(74) Attorney, Agent, or Firm—Henry M. Feiereisen; Ursula B. Day

(57) ABSTRACT

In this method, the refraction performance is either measured along the path of rays (5–7) for a multitude of ray paths which are distributed across a surface, each path originating from one point (P), or is given based on empirically established values. Afterwards the distances of the incident rays between the surfaces intersected by the path of rays are measured along the path or are given based on empirically established values, and the required shape of at least one surface intersected by the paths of rays is calculated based on those values so that the paths of rays intersect in one point as accurately as possible. Based on the values derived in this way optical fittings (3) can be calculated which can be placed on the cornea surface (8–10), inserted into the inner cornea, attached to the anterior section (11) of the eye and inserted into the inner part of the eye in order to simulate arithmetically all measures that change the refraction power of the eye before the measure is actually implemented. As an example a device for the manufacture of an artificial lens (14) is described.

13 Claims, 2 Drawing Sheets

U.S. PATENT DOCUMENTS

| | | | |
|---|---|---|---|
| 4,838,266 | * 6/1989 | Koziol et al. | 128/303.1 |
| 5,092,880 | 3/1992 | Ohmi . | |
| 5,147,393 | 9/1992 | Van Noy . | |
| 5,171,319 | * 12/1992 | Keates et al. | 623/6 |
| 5,179,262 | 1/1993 | Portney . | |
| 5,258,791 | * 11/1993 | Penney et al. | 351/211 |
| 5,282,852 | 2/1994 | Capetan . | |
| 5,325,135 | 6/1994 | Nakamura . | |
| 5,414,478 | 5/1995 | Van Gelderen . | |
| 5,475,453 | 12/1995 | Kuhn . | |
| 5,507,806 | 4/1996 | Blake . | |
| 5,532,770 | 7/1996 | Schneider . | |
| 5,570,142 | * 10/1996 | Lieberman | 351/160 R |
| 5,740,815 | * 4/1998 | Alpins | 128/897 |
| 5,880,809 | * 3/1999 | Lieberman et al. | 351/160 R |
| 5,891,131 | * 4/1999 | Rajan et al. | 606/5 |

FOREIGN PATENT DOCUMENTS

| | | |
|---|---|---|
| 0 264 255A | 4/1988 | (EP) . |
| 0369 561 | 5/1990 | (EP) . |
| 663 179 A1 | 1/1995 | (EP) . |
| 07 34 683 A1 | 3/1996 | (EP) . |
| 13 19 839 | 6/1973 | (GB) . |
| WO 92/01417 | 2/1992 | (WO) . |
| WO 92/17134 | 10/1992 | (WO) . |
| WO 96 35397 | 11/1996 | (WO) . |

\* cited by examiner

METHOD FOR DETERMINING A REQUIRED SHAPE FOR AT LEAST ONE SURFACE OF AN ARTIFICIAL OR NATURAL PART OF AN EYE WHICH IS INTERSECTED BY A PATH OF RAYS THROUGH THE PUPIL OF THE EYE, AND DEVICE FOR THE MANUFACTURE OF AN ARTIFICIAL LENS

BACKGROUND OF THE INVENTION

The invention relates to a method for determining a required shape for at least one surface of an artificial or natural part of the eye which is intersected by a path of rays through the pupil of the eye. The invention also relates to a device for the manufacture of an artificial lens.

The cornea and lens are natural parts of an eye which are intersected by a path of rays passing through the pupil of an eye. In addition to this however, optical fittings can be placed or surgically attached to the surface of the cornea, implants can be inserted into the inner cornea to vary the shape of the cornea, and further fittings can be placed into the anterior section or into the internal part of the eye to refract the path of rays passing through the eye.

The shape of the intersected surfaces is of great importance because the refraction power of the eye is altered by changing the shape of a surface that is intersected by the path of rays. The success of measures for the treatment of natural parts or artificially inserted or attached parts of the eye should be accurately determinable beforehand.

Major problems exist in predicting the success actually achieved, in particular for the coordination of several measures which alter the refraction power of the eye.

It is for example already known when manufacturing an artificial lens, to scan the curvature of the cornea of the eye at 4 points using keratometry, and to determine the approximate curvature of the total cornea surface area using extrapolation. In addition the distances between the anterior surface of the cornea, lens and retina are scanned using biometry to determine the curvature and refraction power of the lens respectively by means of the average curvature of the cornea in such a way that rays which are incident to the cornea, intersect at one point on the retina.

This method is suitable for a cornea with a very uniform curvature. In certain areas of the cornea, incident rays are in practice not focused at the attainable point because the curvature of the cornea, however, is as a rule different over the total area.

In addition, this method is only suitable for determining the surface of an artificial lens.

SUMMARY OF THE INVENTION

The invention faces therefore the task of proposing a method which allows it to determine the required shape of any surface that is intersected by a path of rays through the pupil of an eye, in such a way that an image is created as accurately as possible inside the eye.

This task is resolved using a method through which the refraction performance is measured along the path of rays for a multitude of ray paths which are distributed across the surface, each originating from one point, or is given based on empirically established values, and through which the distances between the surfaces intersected by the path of rays are measured along the path of the incident rays or are given based on empirically established values, and the required shape of at least one surface intersected by the paths of rays is calculated based on those values in such a way that the paths of rays possibly intersect in one point.

The method according to the invention offers the advantage that any number of points can be scanned on a surface intersected by a path of rays through the pupil of the eye in order to increase the accuracy for the shaping of the surface. In especially important areas such as the central area, a lot of points can be calculated whereas in the border area the calculation of only a few points may be sufficient. Also deformations of the cornea or of any other area of the eye that are detected during the scanning or even earlier, can be taken into account using the method according to the invention by scanning in particular many points in this specific area. The required shape determined by this method is therefore adapted accurately to the individual eye and can consequently compensate deformations or irregularities in another part of the eye.

The method is especially suited for the simulation of eye operations. For example, the total surface area of a contact lens placed on the eye surface can be calculated. The use of a contact lens is suitable when the necessary refraction performance of the contact lens is approximately equal on rings which are concentric to the center of the contact lens. Otherwise another measure has to be employed or the surface areas that show discrepancies have to be compensated for by using a further method. This example shows that the method according to the invention can be used as a one stage procedure to determine the required shape of the surface. However, as many required shapes cannot be manufactured due to technical or surgical reasons the refraction performance along the paths of rays is measured again in these cases utilizing a second procedural stage which takes the first measure into account, in order to specify the required shape of another surface based on the measured values.

The different operations for which the accurate determination of the required shape of a surface is of great importance, include—apart from contact lenses - epikeratophakia, photorefractive keratectomy, radiary keratotomy and thermokeratoplastic, intracorneal inlays, intracorneal rings, the lens implantation into the phaco-eye and the use of intraocular lenses.

It is advantageous to choose, in addition to determining the required shape of the surface based on the calculated values, the material of a part of the eye according to its refraction. While the thickness of the substance intersected by the path of rays is taken into account by this method for determining the required shape of the surface, selecting the materials of parts which are artificially inserted into the eye causes a particular refraction performance. The method according to the invention allows it therefore to vary the materials for the parts utilized and to determine the respective shape of the intersected surfaces for different materials. For example, an artificial lens offers a different refraction performance depending on the material used, and another required shape will therefore be specified according to the material utilized using the method according to the invention.

A preferred area of application for this method is presented when attempting to create a device for the manufacture of an artificial lens. The lens manufactured using this method is adapted exactly to the individual cornea of that particular eye and is therefore capable of compensating for deformations on the cornea.

The number of scanned points at which the refraction performance is measured can be increased at will. Preferably more than 20 points should be scanned to achieve an acceptable result.

In order to scan a large number of points it is recommended that the refraction performance at the cornea is analyzed topometrically. The topometry permits a very accurate scanning of the entire cornea surface and is therefore especially suited for the method according to the invention.

The distances along the path of the incident rays between the surfaces intersected by the path of rays such as the cornea, lens and retina, are preferably measured biometrically. This is a simplistic, well researched and particularly precise method for scans such as these.

As it is known that the thickness of the cornea also varies across the surface, it is advantageous to measure the cornea thickness at several points. Normally the thickness of the cornea will not especially be taken into account for the manufacture and also the implantation of artificial lenses. The scanning of the cornea thickness leads however to a further increase in accuracy, for example for the manufacture of artificial lenses.

Depending on the calculation, the point of intersection of the paths of rays can be situated in front of or behind the retina. It is advantageous for the point of intersection to lie on the retina, preferably within the yellow spot.

Principally it is sufficient to calculate a surface to the highest accuracy and reshape it accordingly in order to achieve a single intersection of all paths of rays. In particular for necessarily more involved deformations or in terms of technical manufacturing capability or due to surgical reasons it is however often preferable to calculate the required shapes of several surfaces. For example the anterior or posterior lens part of an artificial lens can be shaped individually so that the total refraction performance of the lens together with the refraction performance of the other surfaces of the eye will lead to the point of intersection created by the method according to the invention.

For humans who require different spectacle lenses to compensate for longsightedness and shortsightedness because of presbyopia, it is recommended that the refraction power of the surfaces is calculated in such a way that a glide sight effect, bifocal or multi-focal effect is created. This can for example be achieved by utilizing special curvatures of an artificially inserted lens.

In addition the invention has the underlying task of proposing a fixture for the manufacture of an artificial lens which makes it possible to take into account uneven patches on the cornea.

This task is resolved using a device for the manufacture of an artificial lens with an input device for entering the cornea curvature and the position of a multitude of points on the cornea as well as the distances between the cornea, the lens to be inserted and the retina using a computer to calculate the refraction angle for each of these points and the curvature of each point matching a point on the cornea on the surface area of the lens, and a device for the manufacture of an artificial lens created based on the calculated values.

Such a device permits the production of an individual lens which compensates for irregularities on the cornea on the basis of the necessary data of a particular eye as determined, for example, by an optician or ophthalmologist. The measured values can for example be transferred to the lens manufacturer on a disk or online who then manufactures a lens according to the predetermined values.

Preferably the device for the manufacture of the artificial lens should include a laser device for cutting the lens. Laser devices allow an exact control of the cutting process and are therefore especially suited to cut an appropriate lens on the basis of predetermined data automatically.

The lens created in this way can be given an identical shape on each radius by using averaging of the values on concentric rings around the center. A higher accuracy can however be achieved when the lens is not shaped concentrically but according to the cornea as accurately as possible.

In this case the lens produced has to be inserted into the human eye with the help of special instruments or suspending fittings in a precisely determined alignment because even a small distortion of the lens ruins the exact adaptation to the cornea. The recommendation therefore is to mark the manufactured lens so that the marking makes the alignment of the lens easier when the lens is inserted.

BRIEF DESCRIPTION OF THE DRAWING

The method according to the invention method and one embodiment of the device according to the invention are displayed in the drawings and are described below in more detail. It is shown in FIG. 1 a horizontal schematic cross-section through the right eyeball viewed from above.

DETAILED DESCRIPTION OF PREFERRED EMBODIMENTS

Figure 1:
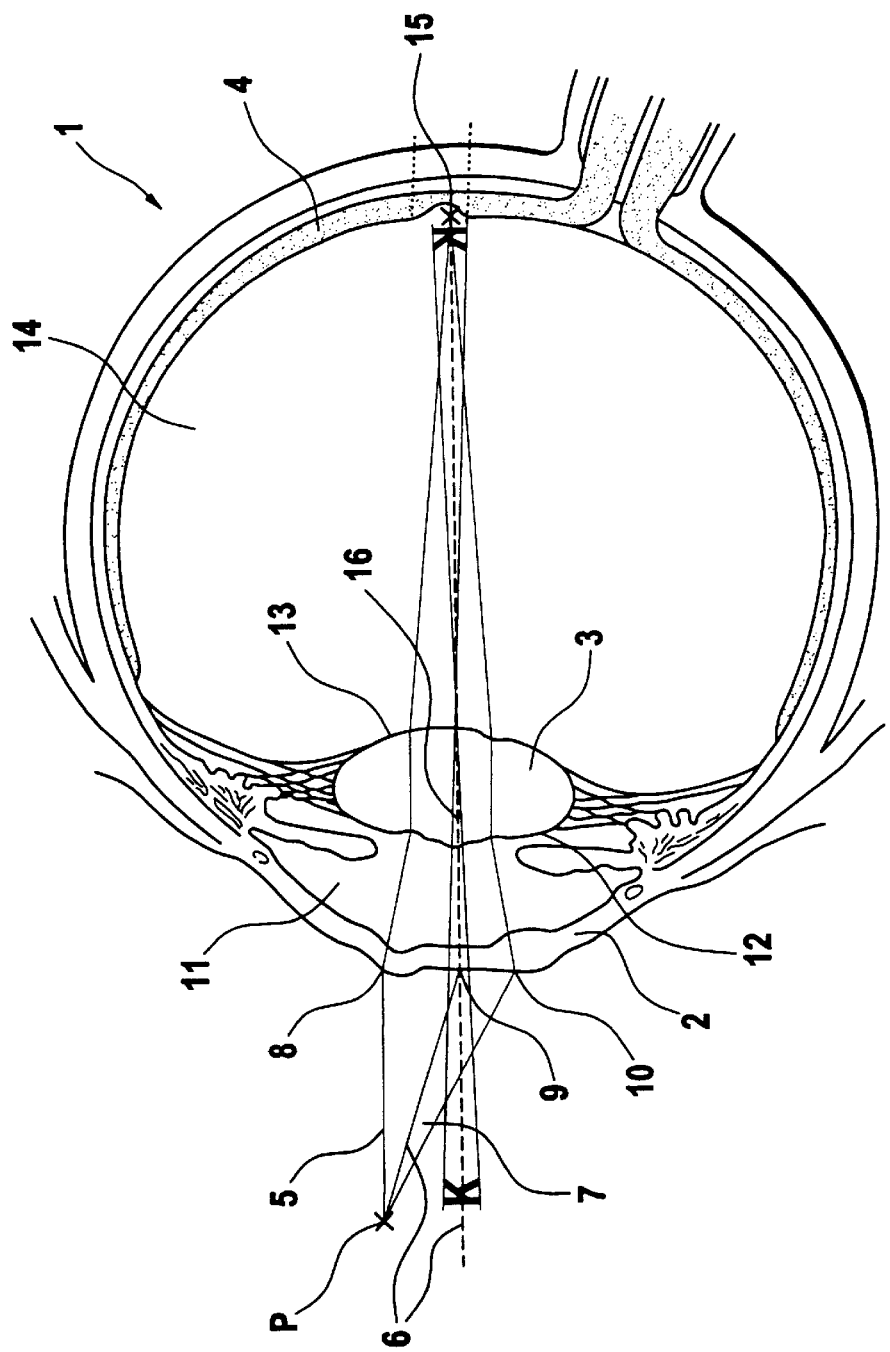

The eye marked 1 displayed in FIG. 1 consists primarily of the cornea 2, the artificial lens 3 and the retina 4. Rays 5, 6, 7 originating from a point P hit the cornea 2 at the points 8, 9, 10, pass through the cornea into the front eye chamber 11, hit the anterior part of the lens 12, pass through the artificial lens 3 and reach the vitreous body 14 via the posterior part of the lens 13. During their further course through the vitreous body rays 5, 6, 7 which emerge from the artificial lens are refracted in such a way that they meet in a common point of intersection 15.

For a spherically curved cornea 2 the curvature of the cornea can for example be measured keratometrically at one or several points in order to determine the curvature of the artificial lens in such a way that the incident rays 5, 6, 7 ideally meet at one point of intersection, in this example the yellow spot 15.

It is however problematic if the cornea 2 as depicted in point 8, shows a deviating curvature or, as depicted in point 10, shows an increased thickness. At these parts of the eye the cornea is not completely spherical, and the incident rays are refracted in such a way that they no longer meet at point 15 after they have passed through the artificial lens. Therefore the invention suggests shaping the lens surfaces 12, 13 in such a way that deviations in terms of the cornea curvature or the cornea thickness can be compensated for by the surface shaping of the artificial lens. In this instance either only one side of the lens can be shaped according to the cornea or the anterior surface 12 and the posterior surface 13, as shown for the path of rays 7, can be varied in such a way that unusual features in the area of the cornea 2 can be compensated for by small changes of the curvatures to the artificial lens. As an example one side of the lens 3 can compensate for the curvature of the cornea and the other side of the lens 3 can compensate for the thickness of the cornea.

In order to calculate the curvature of each point on the lens surface 12, 13 matching point 8, 9, 10 on the cornea 2, it is necessary to scan the distances of incident rays 5, 6, 7 along the path of rays between the cornea 2, the lens to be inserted 3 and the retina 4. These data can be determined using biometry which specifies to an accuracy of a tenth of a millimeter the distances between the cornea 2, anterior surface 12 of the artificial lens 3, posterior surface 13 of the artificial lens 3 and the retina.

When these data are known the exact curvature of the cornea 2 can be determined across the total area of the cornea 2 via a multitude of points 8, 9, 10 using Topometry in order to calculate the refraction angle in each of the points 8, 9, 10. The accuracy of the measurement is further increased by the fact that in addition the thickness of the cornea in each of the points 8, 9, 10 is determined.

Using the values obtained in this way it is aimed to create a device 20 for the manufacture of an artificial lens which produces an artificial lens based on the measured and calculated values.

In the embodiment several thousand points are measured topometrically on the cornea, and the relevant values are calculated in a model. The point of intersection lies on the retina, preferably on the yellow spot. Understandably the curvature of the lens surface, however, can also be calculated in the individual case in such a way that the point of intersection 15 lies on a different part of the retina or in front of or behind the retina.

Using the described method ametropia can be compensated for which can be traced back to a not completely spherical, aspherical or irregular curvature of the incident rays, or to a short or long structure of the eye (axial ametropia). A case of ametropia as a result of an insufficient adaptation of the artificial lens to varying visual ranges is compensated in the present example by an overproportional curvature of the artificial lens 3 in its anterior surface 12 in its central area 16.

The deformations on the cornea 2 and the surfaces 12, 13 of the artificial lens 3 are drawn overproportionally magnified so as to be visible.

Figure 2:
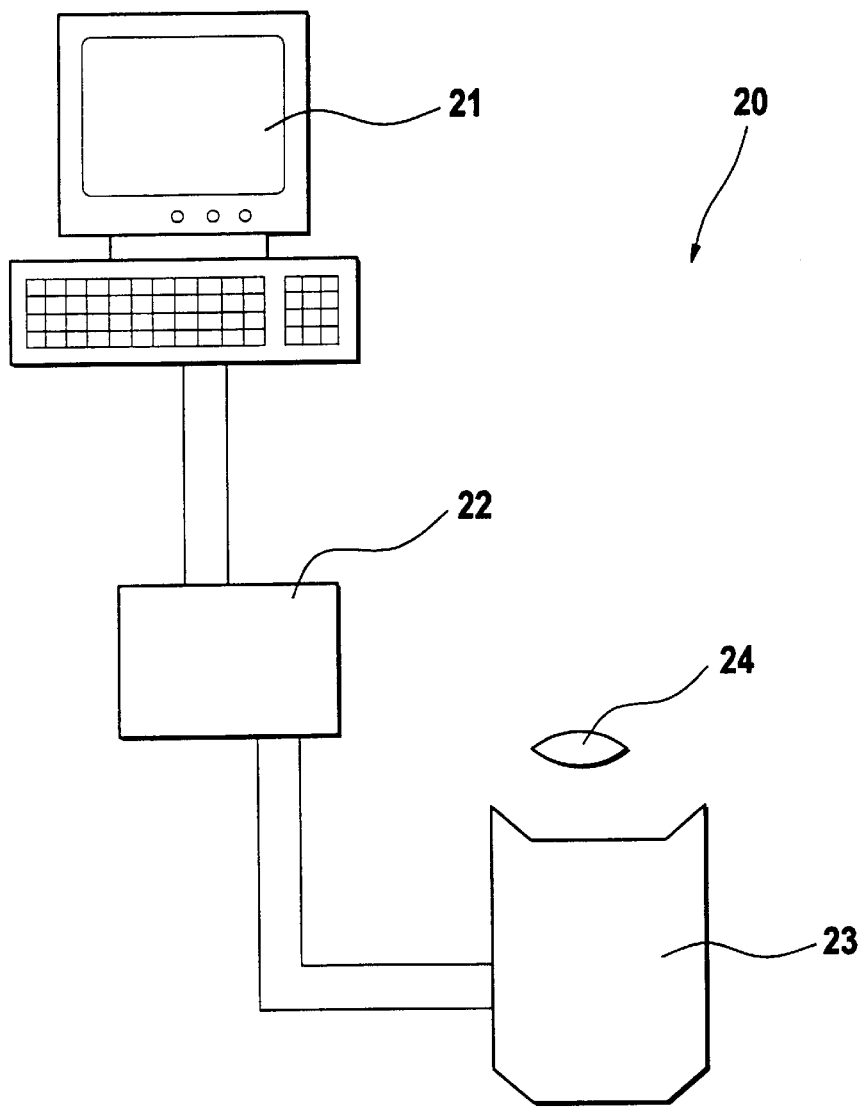
FIG. 2 a schematic display of the device.

FIG. 2 schematically shows an device 20 for cutting an artificial lens 3. This device 20 consists of an input device 21 for entering the cornea curvature and the position of a multitude of points 8, 9, 10 on the cornea 2 as well as the distances between the cornea 2, the lens to be inserted 3 and the retina 4. This input device is suitable for mechanical data entry. However, in addition to this an entry online or via previously labeled data carriers is possible which allows the entry of large amounts of necessary data into the device 20 within the shortest possible time span.

The computer 22 which is connected to the input device has the purpose of determining the refraction angle for each of these points 8, 9, 10 based on the predetermined fixed values and the entered values, and using these to calculate the curvature of each point on the lens surfaces 12, 13 which matches a point on the cornea 2.

These calculated values are then fed into a device 23 for cutting the artificial lens 3 from an optical blank 24 which cuts the lens 3 calculated for individual use from the optical blank 24 using laser devices. A marking 25 is implemented by creating a small notch at the outer lens perimeter 26. This notch does not affect the function of the lens 3. However, it indicates to the surgeon who inserts the lens, how the lens which is adjustable around its central axis 27 has to be aligned.

What is claimed is:

1. method for determining a required shape for at least one surface of an artificial or natural part of the eye which is intersected by a path of rays through the pupil of an eye said method comprising the steps of measuring the refraction performance along the path of rays for a multitude of ray paths which are distributed across the surface, each path originating from one point;

measuring the distances of the incident rays between the surfaces intersected by the path of rays along the path or determining the distances of the incident rays between the surfaces intersected by the path of rays on the basis of empirically established values; and so calculating the required shape of at least one surface intersected by the paths of rays based on those values that the paths of rays intersect in one point.

2. The method of claim 1, wherein the material of parts that are artificially implanted into an eye is selected according to its refraction performance utilizing the calculated values.

3. The method of claim 1, wherein the construction of a device for the manufacture of an artificial lens is attained based on the calculated values.

4. The method of claim 1. wherein the refraction performance is measured at more than 20 points (8, 9, 10).

5. The method of claim 1, wherein the refraction performance at the cornea is analyzed topometrically.

6. The method of claim 1, wherein the distances are measured biometrically.

7. The method of claim 1, wherein the thickness of the cornea is measured at several points (8, 9, 10).

8. The method of claim 1, wherein the point of intersection (15) lies on the retina (4).

9. The method of claim 1, wherein the required shapes of several surfaces (12, 13) are calculated.

10. The method of claim 1, wherein the refraction power of the surfaces (12, 13) is calculated so that one of a glide sight effect, bi-focal and multi-focal effect is created.

11. A device for the manufacture of an artificial lens (3), comprising:

a device (23) for cutting an artificial lens (3) based on [the] calculated values from refraction and distance measurements;

an input device (21) for entering the cornea curvature and the position of a multitude of points (8, 9, 10) on the cornea of the eye (2) as well as the distances between the cornea (2), the lens to be inserted (3) and the retina (4); and a computer (22) for calculating the refraction angle for each of these points (8, 9, 10) and the curvature of each point on the lens surfaces (12, 13) matching a point (8, 9, 10) on the cornea (2) as a starting value for the device (23) for cutting an artificial lens (3).

12. The device of claim 11, wherein the device for cutting an artificial lens (3) includes a laser device.

13. The method of claim 8, wherein the point of intersection (15) lies on the yellow spot of the retina.

* * * * *